United States Patent
Oida et al.

(10) Patent No.: US 6,891,062 B2
(45) Date of Patent: May 10, 2005

(54) PHARMACEUTICAL COMPOSITION FOR TREATMENT OF DISEASES ASSOCIATED WITH DECREASE IN BONE MASS

(75) Inventors: Hiroji Oida, Fukui (JP); Masaharu Tanaka, Fukui (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 25 days.

(21) Appl. No.: 10/844,404

(22) Filed: May 13, 2004

(65) Prior Publication Data

US 2004/0209848 A1 Oct. 21, 2004

Related U.S. Application Data

(62) Division of application No. 10/130,787, filed as application No. PCT/JP00/08235 on Nov. 22, 2000.

(30) Foreign Application Priority Data

Nov. 24, 1999 (JP) ........................................ P. 11-333490
Mar. 1, 2000 (JP) ..................................... P. 2000-56534
Apr. 20, 2000 (JP) .................................... P. 2000-119188

(51) Int. Cl.$^7$ ........................................... C07C 321/00
(52) U.S. Cl. ....................................... 562/426; 514/568
(58) Field of Search ........................... 562/426; 514/568

(56) References Cited

U.S. PATENT DOCUMENTS 5,892,099 A   4/1999   Maruyama et al.

FOREIGN PATENT DOCUMENTS

| EP | 0 855 389 A2 | 7/1998 |
| EP | 0.911 321 A2 | 4/1999 |
| EP | 0 985 663 A1 | 3/2000 |
| GB | 2 330 307 A | 4/1999 |
| JP | 1 097 922 A1 | 5/2001 |
| JP | 1 114 816 A1 | 7/2001 |
| WO | WO 98/27976 | 7/1998 |
| WO | WO 00/21542 | 4/2000 |

OTHER PUBLICATIONS

M. Weinreb, et al., "The anabolic effect of $PGE_2$ in rat bone marrow cultures is mediated via the $EP_4$ receptor subtype," *The American Physiological Society*, Feb. 1999, pp. 376–383.

K. Ono, et al, "Important role of $EP_4$, a subtype of prostaglandin (PG) E receptor, in osteoclast–like cell formation from mouse bone marrow cells induced by $PGE_2$," *Journal of Endocrinology*, vol. 158, No. 3, Sep. 1998, pp. R01–R05.

*Primary Examiner*—Paul J. Killos
(74) *Attorney, Agent, or Firm*—Sughrue Mion, PLLC

(57) ABSTRACT

A pharmaceutical composition for treatment of diseases associated with decrease in bone mass comprising an $EP_4$ agonist as an active ingredient.

An $EP_4$ agonist, in which includes a compound possessing prostaglandin skeleton as a representative, possesses promoting action on bone formation, so it is useful for treatment and/or prevention of diseases associated with decrease in bone mass.

9 Claims, No Drawings

PHARMACEUTICAL COMPOSITION FOR TREATMENT OF DISEASES ASSOCIATED WITH DECREASE IN BONE MASS

CROSS REFERENCE TO RELATED APPLICATIONS

This is a divisional of application Ser. No. 10/130,787 filed May 23, 2002, which is a National Stage Application filed under §371 of PCT Application No. PCT/JP00/08235 filed Nov. 22, 2000.

FIELD OF TECHNOLOGY

The present invention relates to a pharmaceutical composition for treatment of diseases associated with decrease in bone mass comprising an $EP_4$ agonist as an active ingredient.

More detail, it relates to a pharmaceutical composition for treatment and/or prevention of diseases associated with decrease in bone mass such as primary osteoporosis, secondary osteoporosis, metastatic bone, hypercalcemia, Paget's disease, bone loss and osteonecrosis etc., and a pharmaceutical composition for accelerating bone formation such as bone formation after fracture, bone formation after bone grafting, bone formation after operation of artificial joint, bone formation after spinal fusion and bone formation after the other operation for bone regeneration etc. and a pharmaceutical composition for promoting treatment thereof comprising an $EP_4$ agonist as an active ingredient.

RELATED ARTS

Bone repeats a cycle for about 120 to 150 days containing bone resorption by osteoclasts, bone formation by osteoblasts and rest period (called as remodeling). In a normal adult, both bone resorption and bone formation are controlled strictly, so there is little change in a total bone mass. However, in a patient suffering from diseases associated with decrease in bone mass, balance between bone resorption and bone formation is lost and lowering bone mass and deterioration of bone tissue occur. The ratio of lowering bone mass reaches to 20 to 30%. Such a patient tends to experience bone fractures, which sometimes causes a bedridden condition, deformation of body, or death in worst case wherein fractures occurs at the risky position such as coxa etc.

A representative disease associated with decrease in bone mass includes osteoporosis. Osteoporosis is a systemic disease characterized by lowering bone mass and deterioration of bone tissue as a main symptom.

There may be various causes of osteoporosis and most frequent cause is said to be aging, especially postmenopausal hormone unbalance in women. Therefore, at present, administration of estrogen, vitamin D or calcitonin has been carried out as a main treatment of osteoporosis. However, there is a risk to induce a cancer (especially, breast cancer, uterine cancer etc.) in hormone-treatment, so such a treatment is not safe one.

Further, administration of bisphosphonate as a second-generation medicament has been carried out. However, there is a problem that interruption of administration may cause rebound.

In addition, even if it may be possible to delay the aggravation of osteoporosis by the mentioned treatment, it is difficult to regenerate the bone which has decreased once.

On the other hand, prostaglandin $E_2$ (abbreviated as $PGE_2$) is known as a metabolite in an arachidonic acid cascade. It is known that it possess various activities such as cyto-protective activity, uterine contractile activity, a pain-inducing effect, a promoting effect on digestive peristalsis, an awakening effect, a suppressive effect on gastric acid secretion, hypotensive activity and diuretic activity etc.

$PGE_2$ is said to relate to bone resorption (J. Dent Res. 59(10), 1635 (1980); Nature 266, 6455 (1977)).

Further, there was a patent application disclosed that growth of bone tissue and increase of bone mass were seen macroscopically or microscopically in a dog to which $PGE_1$ or $PGE_2$ was administered orally or intravenously. But, each dose was 1000 µg/kg/day, which is a much high dose as PG, so it is uncertain that each said PG plays an essential role. It may be difficult to obtain a practical agent in view of such a high dose.

A recent study has proved existence of various $PGE_2$ receptor subtypes possessing a different physical role from each other. At present, four receptor subtypes are known and they are called $EP_1$, $EP_2$, $EP_3$, $EP_4$ (Negishi M. et al, J. Lipid Mediators Cell Signaling 12, 379–391 (1995)). It has become possible to obtain an agent causing less side effect by studying a role of each receptor subtype and by finding out the compound which can bind to each receptor specifically and can not bind any other receptors.

Recently, it is disclosed that an $EP_2$ agonist and an $EP_4$ antagonist are useful for treatment of osteoporosis (WO98/279769) and accelerated bone resorption (GB2,330,307), respectively.

Further, it is described that a compound of the formula (IA) is useful as a conjugator to an $EP_4$ receptor in EP-855389. This patent application shows that a compound of the formula (IA) is useful for treatment and prevention of bone formation disorder. However, it is neither described nor suggested that which $EP_4$ agonist or $EP_4$ antagonist relates to bone formation or what role in such a treatment.

As mentioned above, there is a suggestion that $PGE_2$ or $PGE_1$ relates to bone metabolites and that some subtypes of them relates to it really. However, it is uncertain that which subtypes of them, or which antagonist or agonist is useful concretely.

DISCLOSURE OF THE INVENTION

The present inventors et al. have synthesized various compounds which can bind to each PGE receptor subtype selectively and examined them in order to find out the compounds possessing bone formation activity as a treating agent for diseases associated with decrease in bone mass.

Until now, it has been thought that an $EP_4$ antagonist is useful for treatment of diseases associated with decrease in bone mass because of its inhibitory action on bone resorption, but that an $EP_4$ agonist is not useful for such a treatment because of promoting action on bone resorption which may cause a decrease of bone mass. However, unexpectedly, we have found that an $EP_4$ agonist at a low dose causes an increase of bone mass and bone density, and then completed the present invention.

In addition, it has been confirmed that the later mentioned compounds of the formulae (IA) to (IJ) which are representative $EP_4$ agonists possess an $EP_4$ agonistic action according to experiments.

The present invention relates to a pharmaceutical composition for treatment and/or prevention of diseases associated with decrease in bone mass comprising an $EP_4$ agonist as an active ingredient.

According to the present invention, it has been confirmed first that an $EP_4$ agonist possesses action on increasing bone mass and bone density, and promoting action on bone formation.

In the present invention, diseases associated with decrease in bone mass means disease followed by conditions such as lowering bone density, deterioration of bone tissue etc. and includes, for example, 1) primary osteoporosis (e.g., primary osteoporosis followed by aging, postmenopausal primary osteoporosis, primary osteoporosis followed by ovariectomy etc.),
2) secondary osteoporosis (e.g., glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, rheumatoid osteoporosis etc.),
3) bone diseases such as metastatic bone, hypercalcemia, Paget's disease, bone loss (alveolar bone loss, mandibular bone loss, childhood idiopathic bone loss etc.), osteonecrosis etc.

Besides treatment of the above diseases, the present invention also includes a pharmaceutical composition for accelerating bone formation after bone operation (e.g., bone formation after fractures, bone formation after bone grafting, bone formation after operation of artificial joint, bone formation after spinal fusion and bone formation after the other operation for bone regeneration etc.), or promoting treatment thereof, or alternative treatment for bone grafting.

In the present invention, an $EP_4$ agonist means every compound which can bind to $EP_4$ receptor subtype of $PGE_2$ receptors selectively, can not or do not bind any other $EP_1$, $EP_2$, $EP_3$ receptor subtypes, and possesses $EP_4$ agonistic action.

Therefore, such compounds include $EP_4$ agonists which will be found newly in future as well as known ones at present. In addition, such $EP_4$ agonists include compounds possessing non-PG skeleton as well as PG skeleton.

These compounds can bind an $EP_4$ receptor selectively, and they do not induce pain may be caused by $EP_1$, uterine relaxation may be caused by $EP_2$ and uterine contraction may be caused by $EP_3$ at all, so they are agents having no effect on the above actions.

As shown in the experiments mentioned later, an $EP_4$ agonist possesses a strong promoting action on bone formation, so it is useful for treatment of the mentioned diseases associated with decrease in bone mass such as osteoporosis.

The preferred compounds used in the present invention are as follows: For example, the compounds selected from $EP_4$ agonists consisting of the compounds the formula (IA)

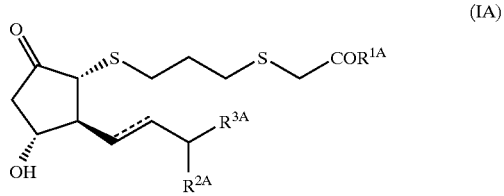

(IA)

(wherein $R^{1A}$ is hydroxy, C1–4 alkyloxy, or $NR^{6A}R^{7A}$ (in which each $R^{6A}$ and $R^{7A}$ is independently hydrogen or C1–4 alkyl),
$R^{2A}$ is hydrogen or hydroxy,
$R^{3A}$ is
(i) C1–8 alkyl, C2–8 alkenyl, or C2–8 alkynyl,
(ii) phenyl or C3–7 cycloalkyl,
(iii) C1–8 alkyl, C2–8 alkenyl or C2–8 alkynyl substituted by phenyl or C3–7 cycloalkyl (with the proviso that when $R^{2A}$ is hydrogen; alkyl, alkenyl and alkynyl in (i) and (ii) may be substituted by one hydroxy), symbol ══ is double bond or single bond. With the proviso that 8-epi equilibrium compound thereof is included), the compounds of the formula (IB)

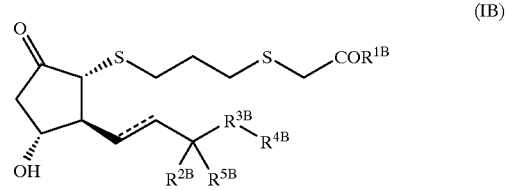

(IB)

(wherein $R^{1B}$ is hydroxy, C1–6 alkyloxy, or $NR^{6B}R^{7B}$ (in which each $R^{6B}$ and $R^{7B}$ is independently hydrogen or C1–6 alkyl),
$R^{2B}$ is hydrogen or hydroxy,
$R^{3B}$ is single bond or C1–6 alkylene,
$R^{4B}$ is
(i) C1–8 alkyl, C2–8 alkenyl, or C2–8 alkynyl substituted by one to three group selected from C1–6 alkyloxy or halogen,
(ii) phenyloxy or C3–7 cycloalkyloxy,
(iii) furyl, furyloxy, thienyl, thienyloxy, naphthyl, naphthyloxy, phthalanyl, or phthalanyloxy,
(iv) phenyl, phenyloxy, C3–7 cycloalkyl, or C3–7 cycloalkyloxy substituted by one to three group selected from the following group:
C1–6 alkyl,
C2–6 alkenyl,
C2–6 alkynyl,
C1–6 alkyloxy,
C1–6 alkyloxy-C1–6 alkyl,
C1–6 alkyloxy-C1–6 alkyloxy,
C2–6 alkenyloxy-C1–6 alkyl,
C1–6 alkyl substituted by one to three hydroxy,
C1–6 alkyl substituted by one to three halogen,
C1–6 alkylthio,
C1–6 alkylthio-C1–6 alkyl,
C1–6 alkylthio-C1–6 alkyloxy,
C2–6 alkenylthio-C1–6 alkyl,
C1–6 alkylsulfonyl,
halogen,
trihalomethyl,
cyano,
nitro,
amino,
hydroxy,
C3–7 cycloalkyl,
C3–7 cycloalkyloxy,
C3–7 cycloalkyl-C1–6 alkyl,
C3–7 cycloalkyloxy-C1–6 alkyl,
phenyl,
phenyloxy,
phenyl-C1–6 alkyl,
phenyl-C2–6 alkenyl,
phenyl-C2–6 alkynyl,
phenyloxy-C1–6 alkyl,
phenyloxy-C2–6 alkenyl,
phenyloxy-C2–6 alkynyl, furyl,
furyloxy,
furyl-C1–6 alkyl,
furyloxy-C1–6 alkyl,
thienyl,
thienyloxy,
thienyl-C1–6 alkyl, or
thienyloxy-C1–6 alkyl
(the above mentioned phenyl, furyl, thienyl or cycloalkyl may be substituted by one to three group selected from C1–6 alkyl, C1–6 alkyloxy, C1–6 alkyloxy-C1–6 alkyl, nitro, halogen, trihalomethyl, amino and hydroxy); or
(v) furyl, furyloxy, thienyl, thienyloxy, naphthyl, naphthyloxy, phthalanyl, or phthalanyloxy substituted by one to three group selected from the following group:
C1–6 alkyl,
C2–6 alkenyl,
C2–6 alkynyl,
C1–6 alkyloxy,
C1–6 alkyloxy-C1–6 alkyl,
C1–6 alkyloxy-C1–6 alkyloxy,
C2–6 alkenyloxy-C1–6 alkyl,
C1–6 alkyl substituted by one to three hydroxy,
C1–6 alkyl substituted by one to three halogen,
C1–6 alkylthio,
C1–6 alkylthio-C1–6 alkyl,
C1–6 alkylthio-C1–6 alkyloxy,
C2–6 alkenylthio-C1–6 alkyl,
C1–6 alkylsulfonyl,
halogen,
trihalomethyl,
cyano,
nitro,
amino,
hydroxy,
C3–7 cycloalkyl,
C3–7 cycloalkyloxy,
C3–7 cycloalkyl-C1–6 alkyl,
C3–7 cycloalkyloxy-C1–6 alkyl,
phenyl,
phenyloxy,
phenyl-C1–6 alkyl,
phenyl-C2–6 alkenyl,
phenyl-C2–6 alkynyl,
phenyloxy-C1–6 alkyl,
phenyloxy-C2–6 alkenyl,
phenyloxy-C2–6 alkynyl,
furyl,
furyloxy,
furyl-C1–6 alkyl,
furyloxy-C1–6 alkyl,
thienyl,
thienyloxy,
thienyl-C1–6 alkyl, or
thienyloxy-C1–6 alkyl
(the above mentioned phenyl, furyl, thienyl or cycloalkyl may be substituted by one to three group selected from C1–6 alkyl, C1–6 alkyloxy, C1–6 alkyloxy-C1–6 alkyl, nitro, halogen, trihalomethyl, amino and hydroxy), $R^{5B}$ is hydrogen or C1–6 alkyl,
symbol ══ is double bond or single bond.

With the proviso that when $R^{2B}$ is hydrogen, C1–6 alkylene represented by $R^{3B}$ may be substituted by one hydroxy, and that 8-epi equilibrium compound thereof is included), the compounds of the formula (IC)

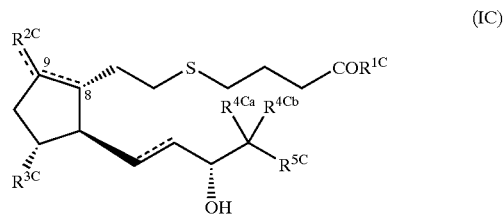

(IC)

(wherein $R^{1C}$ is hydroxy, C1–6 alkyloxy, or $NR^{6C}R^{7C}$ (in which each $R^{6C}$ and $R^{7C}$ is independently hydrogen or C1–4 alkyl), $R^{2C}$ is oxo, halogen, or $O-COR^{8C}$ (in which $R^{8C}$ is C1–4 alkyl, phenyl, or phenyl(C1–4 alkyl)), $R^{3C}$ is hydrogen or hydroxy, each $R^{4Ca}$ and $R^{4Cb}$ is independently hydrogen or C1–4 alkyl, $R^{5C}$ is phenyl substituted by the following group:

(i) one to three group selected from
C1–4 alkyloxy-C1–4 alkyl,
C2–4 alkenyloxy-C1–4 alkyl,
C2–4 alkynyloxy-C1–4 alkyl,
C3–7 cycloalkyloxy-C1–4 alkyl,
C3–7 cycloalkyl(C1–4 alkyloxy)-C1–4 alkyl,
phenyloxy-C1–4 alkyl,
phenyl-C1–4 alkyloxy-C1–4 alkyl,
C1–4 alkylthio-C1–4 alkyl,
C2–4 alkenylthio-C1–4 alkyl,
C2–4 alkynylthio-C1–4 alkyl,
C3–7 cycloalkylthio-C1–4 alkyl,
C3–7 cycloalkyl(C1–4 alkylthio)-C1–4 alkyl,
phenylthio-C1–4 alkyl, or
phenyl-C1–4 alkylthio-C1–4 alkyl, (ii) C1–4 alkyloxy-C1–4 alkyl and C1–4 alkyl,
C1–4 alkyloxy-C1–4 alkyl and C1–4 alkyloxy,
C1–4 alkyloxy-C1–4 alkyl and hydroxy,
C1–4 alkyloxy-C1–4 alkyl and halogen,
C1–4 alkylthio-C1–4 alkyl and C1–4 alkyl,
C1–4 alkylthio-C1–4 alkyl and C1–4 alkyloxy,
C1–4 alkylthio-C1–4 alkyl and hydroxy, or
C1–4 alkylthio-C1–4 alkyl and halogen, (iii) haloalkyl or hydroxy-C1–4 alkyl, or
(iv) C1–4 alkyl and hydroxy;
symbol ══ is single bond or double bond.

With the proviso that when $R^{2C}$ is $O-COR^{8C}$ bond between 8- and 9-position is double bond), and the compounds of the formula (ID)

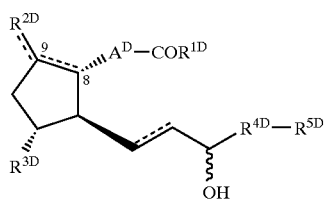

(wherein $A^D$ is C2–8 alkylene, C2–8 alkenylene, C1–4 alkylene-phenylene, or C2–4 alkenylene-phenylene, $R^{1D}$ is hydroxy, C1–6 alkyloxy, C1–6 alkyloxy-C1–6 alkyloxy, HO—C1–6 alkyloxy, or $NR^{6D}R^{7D}$ (in which each $R^{6D}$ and $R^{7D}$ is independently hydrogen or C1–4 alkyl), $R^{2D}$ is oxo, halogen, or $R^{8D}$—COO—(in which $R^{8D}$ is hydrogen, C1–4 alkyl, phenyl, phenyl(C1–4 alkyl), C1–4 alkyloxy, HOOC—C1–4 alkyl, C1–4 alkyloxy-carbonyl-C1–4 alkyl, HOOC—C2–4 alkenyl, or C1–4 alkyloxy-carbonyl-C2–4 alkenyl), $R^{3D}$ is hydrogen or hydroxy, $R^{4D}$ is C1–4 alkylene, $R^{5D}$ is phenyl substituted by the following group:

(i) one to three group selected from

C1–4 alkyloxy-C1–4 alkyl,
C2–4 alkenyloxy-C1–4 alkyl,
C2–4 alkynyloxy-C1–4 alkyl,
C3–7 cycloalkyloxy-C1–4 alkyl,
C3–7 cycloalkyl(C1–4 alkyloxy)-C1–4 alkyl,
phenyloxy-C1–4 alkyl,
phenyl-C1–4 alkyloxy-C1–4 alkyl,
C14 alkylthio-C1–4 alkyl,
C2–4 alkenylthio-C1–4 alkyl,
C2–4 alkynylthio-C1–4 alkyl,
C3–7 cycloalkylthio-C1–4 alkyl,
C3–7 cycloalkyl(C1–4 alkylthio)-C1–4 alkyl,
phenylthio-C1–4 alkyl or
phenyl-C14 alkylthio-C1–4 alkyl, (ii) C1–4 alkyloxy-C1 alkyl and C1–4 alkyl, C1–4 alkyloxy-C1–4 alkyl and C1–4 alkyloxy,
C1–4 alkyloxy-C1–4 alkyl and hydroxy,
C1–4 alkyloxy-C1–4 alkyl and halogen,
C1–4 alkylthio-C-1–4 alkyl and C1–4 alkyl,
C1–4 alkylthio-C1–4 alkyl and C1–4 alkyloxy,
C1–4 alkylthio-C1–4 alkyl and hydroxy, or
C1–4 alkylthio-C1–4 alkyl and halogen, (iii) halo-C1–4 alkyl or hydroxy-C1–4 alkyl or
(iv) C1–4 alkyl and hydroxy;

symbol ===== is single bond or double bond.

With the proviso that when $R^{2D}$ is the formula $R^{8D}$—COO—, $R^{1D}$ is C1–6 alkyloxy, C1–6 alkyloxy-C1–6 alkyloxy, or HO—C1–6 alkyloxy, bond between 8- and 9-position is double bond).

The more preferable compounds used in the present invention as an $EP_4$ agonist are as follows: (parentless under each formula shows patent publication or application number and example number).

For example, prostaglandin derivatives of the formula (IE)

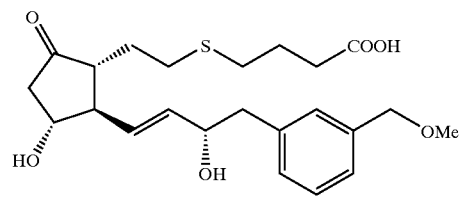

(WO00/03980, Example 3),
the formula (IF)

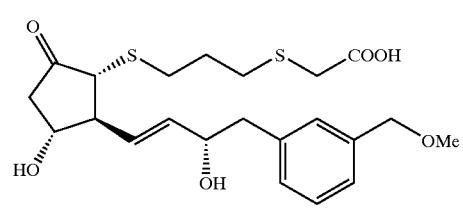

(EP-985663, Example 2),
the formula (IG)

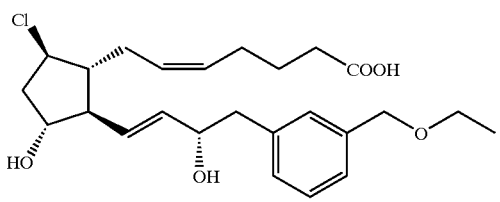

(PCT/JP99/04934, Example 8-6),
the formula (IH)

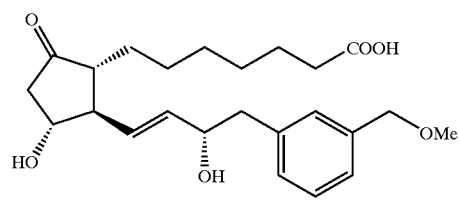

(PCT/JP99/04934, Example 2)
and the formula (IJ)

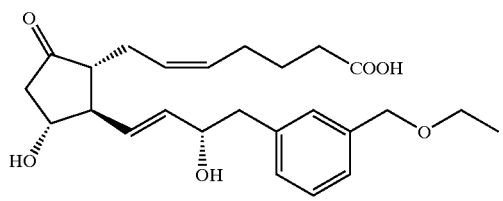

(PCT/JP99/04934, Example 2-11)
or alkyl ester thereof, non-toxic salt thereof and cyclodextrin clathrate thereof.

[Ester]

The compounds of the present invention shown by the formulae (IA) to (IJ) may be converted into esters by known method. Converting into the corresponding esters serves to increase the stability and absorbaility of the compounds, and therefore it is useful in the use for pharmaceuticals. An alkyl ester is preferred, C1–4 alkyl ester is more preferable and methyl ester is most preferable.

[Salt]

The compounds of the present invention shown by the formulae (IA) to (IJ) may be converted into the corresponding salts by known methods. Non-toxic and water-soluble salts are preferable. Suitable salts, for example, are as follows: salts of alkali metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl) amine, lysine, arginine, N-methyl-D-glucamine etc.). The compounds of the present invention shown by the formulae (IA) to (IJ) may be converted into the corresponding hydrates by known methods.

[Clathrate]

The compounds of the present invention shown by the formulae (IA) to (IJ), and ester thereof may be converted into the corresponding cyclodextrin clathrates by the method described in the specification of GB1,351,238 or GB1,419,221 using $\alpha$-, $\beta$- or $\gamma$-cyclodextrin or a mixture thereof. Converting into the corresponding cyclodextrin clathrates serves to increase the stability and solubility in water of the compounds, and therefore it is useful in the use for pharmaceuticals.

[Process for Preparation of a Compound of the Present Invention]

Each compound of the formulae (IA) to (IJ) and a process for preparation thereof is described in the following patent applications.

a compound of the formula (IA): EP-855389,
a compound of the formula (IB): EP-985663,
a compound of the formula (IC): WO00/03980,
a compound of the formula (ID): Application No. PCT/JP99/04934,
a compound of the formula (IE): WO00/03980,
a compound of the formula (IF): EP-985663,
a compound of the formula (IG): Application No. PCT/JP99/04934,
a compound of the formula (IH): Application No. PCT/JP99/04934,
a compound of the formula (IJ): Application No. PCT/JP99/04934.

BEST MODE TO CARRY OUT THE INVENTION

The following Reference Examples and Examples are intended to illustrate, but not limit the present invention.

EXAMPLE 1

Promoting Action on Bone Formation

Beagle/CSK strain dogs of 6-month old were used (n=3 to 6 per group).

Into a physical saline solution, each (11 $\alpha$, 15 $\alpha$, 13E)-9-oxo-11,15-dihydroxy-16-(3-methoxymethylphenyl)-17,18,19,20-tetranor-5-t hiaprost-13-enoic acid methyl ester (methyl ester of a compound of the formula (IE)) $\alpha$-cyclodextrin clathrate (containing rate of an active ingredient in $\alpha$-cyclodextrin clathrate form is 25% w/w), (11 $\alpha$, 15 $\alpha$, 13E)-9-oxo-11,15-dihydroxy-16-(3-methoxymethylphenyl)-17,18,19,20-tetranor-3,7-dithiaprost-13-enoic acid (a compound of the formula (IF)), (9$\beta$, 11 $\alpha$, 15 $\alpha$, 5Z, 13E)-9-chloro-11,15-dihydroxy-16-(3-ethoxymethylphenyl)-17,18,19,20-tetranopro st-5,13-dienoic acid (a compound of the formula (IG)), (11 $\alpha$, 15 $\alpha$, 13E)-9-oxo-11,15-dihydroxy-16-(3-methoxymethylphenyl)-17,18,19,20-tetranorpro st-13-enoic acid (methyl ester of a compound of the formula (IH)), and (11 $\alpha$, 15 $\alpha$, 5Z, 13E)-9-oxo-11,15-dihydroxy-16-(3-ethoxymethylphenyl)-17,18,19,20-tetranorprost-5,13-dienoic acid (a compound of the formula (IJ)) was dissolved, and administered continuously to each animal at the effective doses of 2, 5, 10 and 25 $\mu$g/kg/day, for 24 hours per day during 4 weeks. Each test solution was administered into femoral vein through holding-catheter at the rate of 0.2 ml/kg/hour. An equal volume of physical saline solution was administered into an animal of the control group. After termination of administration, each animal was sacrificed to carry out autopsy.

(1) Determination of Bone Area

The separated femur was fixed with 10% buffered formalin solution and then was cut into a round slice with the width of 10 mm vertically to longitudinal axis at the 25 mm central side from trochlea sulcus. Pictures of bone surface near side of epiphysis were taken with camera connected to the computer from the constant distance, and then the resulted digital image was analyzed to determine bone area.

The results were shown in the following Table 1.

TABLE 1

| Test solution | Dose ($\mu$g/kg/day) | bone area (mm$^2$) |
| --- | --- | --- |
| Untreated control n = 6 | 0 | 68.93 ± 6.64 |
| Invention compound (IE) n = 6 | 2 | 77.96 ± 6.94 |
| Invention compound (IE) n = 6 | 10 | 190.69 ± 19.03*** |
| Invention compound (IE) n = 4 | 25 | 502.76 ± 54.81*** |
| Invention compound (IF) n = 3 | 5 | 365.29 ± 73.63 |
| Invention compound (IG) n = 3 | 10 | 140.10 ± 28.08 |
| Invention compound (IG) n = 3 | 25 | 289.38 ± 120.50 |
| Invention compound (IH) n = 3 | 5 | 362.99 ± 89.56 |
| Invention compound (IJ) n = 3 | 5 | 193.23 ± 11.32 |

***p < 0.001 (indicating a significant difference in Dunnett-test)

Discussion:

Invention Group of the present compound of the formula (IE) at the doses of 10 $\mu$g/kg/day or more showed 2.8-fold increase of bone area to compare with Untreated Group. Especially, more than 7-fold increase of bone area was seen in Invention Group at the dose of 25 $\mu$g/kg/day.

Invention Group of the present compounds of the formulae (IF), (IH) and (IJ) at the dose of 5 $\mu$g/kg/day also showed 2.8–5.3 fold increase of bone area to compare with Untreated Group. In addition, Invention Group of the present compound of the formula (IG) at the dose of 25 $\mu$g/kg/day also showed 4.2 fold increase of bone area to compare with Untreated Group.

(2) Determination of Bone Density

After taking radiographs of the sample with width of 1 cm used in the above (1) from the side, the resulted graphs input was sent to computer to assay radiation level per unit area with constant width and to determine bone density (Microfocus X-ray System μ FX-1000 (Fuji Photo Film Co., Ltd.)). The results were shown in Table 2.

TABLE 2

| Test solution | Dose (μg/kg/day) | Bone density (PSL/mm²) |
|---|---|---|
| Untreated control n = 6 | 0 | 5.93 ± 0.72 |
| Invention compound (IE) n = 6 | 2 | 5.63 ± 0.70 |
| Invention compound (IE) n = 6 | 10 | 8.75 ± 1.19*** |
| Invention compound (IE) n = 4 | 25 | 10.34 ± 1.58*** |

***p < 0.001 (indicating a significant difference in Dunnett-test)

Discussion:

Invention Group of the present compound of the formula (IE) at the doses of 10 and 25 μg/kg/day showed 1.5-fold and 1.7-fold increase of bone density to compare with Untreated Group, respectively. From these results, it has been confirmed that the present compounds which are $EP_4$ agonists induce a significant increase of bone area and bone density at the dose of 10 μg/kg/day or more and possess promoting action on bone formation.

EXAMPLE 2

Determination of $EP_4$ Agonistic Action

It has been confirmed that compounds of the formulae (IA) to (IJ) can bind to $EP_4$ receptor and that they show an $EP_4$ agonistic action by the following experiments.

The agonistic activity of compounds of the formulae (IA) to (IJ) was determined by using CHO cells which have expressed an $EP_4$ receptor (to see FEBS Letters 364, 339 (1995) with modification in part). Then, it has been confirmed that all compounds cause increase of cAMP level and that they are $EP_4$ agonists.

EXAMPLE 3

Promoting Action on Bone Formation

Experimental Method:

SD strain female rats of 11-week old (n=8, average of body weight is 271 g) were used. Incision was made on the side abdominal part of rat under pentobarbital anesthesia to carry out ovariectomy and then the region of incision was sutured. Only incision and suture were made on the animals in Sham Group without ovariectomy.

Since on the 6-day after ovariectomy, a solution prepared by dissolving (11 α, 5 α, 13E)-9-oxo-11,15-dihydroxy-16-(3-methoxymethyl-phenyl)-17,18,19,20-tetranor-5-thiaprost-13-enoic acid methyl ester (a methyl ester of compound of the formula (IE)) α-cyclodextrin clathrate (containing rate of active ingredient in a cyclodextrin clathrate is 25% w/w) into a physical saline solution had been administered subcutaneously into poll of each animal at the dose of 30 μg/5 ml/kg every 8 hours, total three times per day, for 2 months. In Control Group and Sham Group, a physical saline solution was administered to each animal. After termination of experiment, each animal was sacrificed to carry out autopsy. Bone density of cancellous bone region of left femur was determined using equipment for assaying distal bone density (XCT-960A, Norland/Stolatec Co.). The results were shown in the following Table.

TABLE 3

| Group | Bone density (mg/cm³) Means ± SD |
|---|---|
| Sham Group | 404.1 ± 87.0 |
| Control Group | 226.3 ± 38.9### |
| Invention compound (IE) Group | 794.0 ± 50.2*** | p < 0.001 vs Sharm Group
***p < 0.001 vs Control Group
(both: T-test)

Discussion:

As shown in Table 3 clearly, Invention Compound Group showed a significant increase of bone density to compare with Control Group (non-administration).

[Toxicity]

The toxicity of the compounds of the formula (IE) of the present invention is very low and therefore, it is confirmed that these compounds are safe for use as medicine. For example, the maximum tolerance dose of the compound of the formula (IE) by i.v. route in rat was 30 mg/kg body weight or more.

INDUSTRILA APPLICATION

[Application for Pharmaceuticals]

An $EP_4$ agonist used in the present invention possesses a promoting action on bone formation, so it is useful for treatment and/or prevention of diseases associated with decrease in bone mass. In the present invention, diseases associated with decrease in bone mass means disease which occurs diseases associated with decrease in bone mass followed by lowering bone density, or by deterioration of bone tissue etc. For example, such a disease includes:

1) primary osteoporosis (e.g., osteoporosis followed by aging, postmenopausal primary osteoporosis, osteoporosis followed by ovariectomy etc.),
2) secondary osteoporosis (e.g., glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, rheumatoid osteoporosis etc.),
3) bone diseases such as metastatic bone, hypercalcemia, Paget's disease, bone loss (alveolar bone loss, mandibular bone loss, childhood idiopathic bone loss etc.), osteonecrosis etc.

In addition, the present invention includes accelerating bone formation after operation for bone (e.g., bone formation after fracture, bone formation after bone grafting, bone formation after operation for artificial joint, bone formation after spinal fusion and bone formation after the other bone regeneration etc.) and promoting treatment thereof, and alternative treatment for bone grafting.

For the purpose above described, an $EP_4$ agonist, ester thereof, non-toxic salt thereof or cyclodextrin clathrate thereof used in the present invention, may be normally administered locally, by oral or parenteral administration. Converting into a prodrug serves to diminish irritation and improve absorpability and stability etc.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1

μg and 10 mg, preferably between 0.2 mg and 5 mg, by parenteral administration (preferred by endermic route, by subcutaneous route or into vein) up to several times per day.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, or as injections, endermic ointments, patches or suppositories etc. for parenteral administration.

Solid compositions for oral administration include compressed tablets, pills, capsules, dispersible powders, and granules etc.

Capsules contain hard capsules and soft capsules.

In such solid compositions, one or more of the active compound(s) is or are, admixed with at least one inert diluent such as lactose, mannitol, mannit, glucose, hydroxypropyl cellulose, N microcrystalline cellulose, starch, polyvinylpyrrolidone, magnesium metasilicate aluminate.

The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol). Besides inert diluents, such compositions may also comprise adjuvants such as wetting agents, suspending agents, sweetening agents, flavoring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSORBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They may also be manufactured in the form of sterile solid compositions which can be dissolved in sterile water or some other sterile diluent for injection immediately before use.

Other compositions for parenteral administration include liquids for external use, ointments, liniments, patches and suppositories etc. which comprise one or more of the active compound(s) and may be prepared by known methods.

Ointment may include pH-adjustfied agents, surfactant, preserving agents, emulsifying agents, dispersing agents, stabilizing agent, assisting agents for dissolving etc. in addition to basic such as white vaseline.

FORMULATION EXAMPLE 1

Freeze-Dried Formulation

The following components were admixed by a conventional method, and the solution was sterilized by a conventional method, placed 1 ml portions into ampoules and freeze-dried by a conventional method to obtain 100 ampoules each containing 0.2 mg of active ingredient.

| | |
|---|---|
| (11α,15α,13E)-9-oxo-11,15-dihydroxy-16-(3-methoxymethylphenyl)-17,18,19,20-tetranor-5-thiaprost-13-enoic acid methyl ester α-cyclodextrin | 80 mg (active ingredient: 20 mg) |
| mannit | 5 g |
| distilled water | 100 ml |

FORMULATION EXAMPLE 2

Ointment

The following components were admixed by a conventional method and placed each 10 g of the mixture into tube to obtain 100 tubes of ointment each containing 0.2 mg of active ingredient per 1 g of mixture.

| | |
|---|---|
| (11α,15α,13E)-9-oxo-11,15-dihydroxy-16-(3-methoxymethylphenyl)-17,18,19,20-tetranor-5-thiaprost-13-enoic acid methyl ester α-cyclodextrin | 800 mg (active ingredient: 200 mg) |
| white vaseline | 1 kg |

What is claimed is:

1. A method of treatment and/or prevention of a disease associated with a decrease in bone mass comprising, administering to a patient in need of treatment an effective amount of a compound of formula (I),

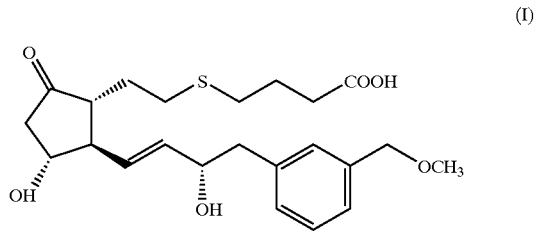

non-toxic salt, methyl ester, or α-cyclodextrin clathrate thereof.

2. A method of treatment and/or prevention of a disease associated with a decrease in bone mass comprising, administering to a patient in need of treatment an effective amount of a (11 α, 15 α, 13E)-9-oxo-11,15-dihydroxy-16-(3-methoxymethylphenyl)-17, 18, 19, 20-tetranor-5-thiaprost-13-enoic acid methyl ester α-cyclodextrin clathrate.

3. The method according to claim 1 or 2, wherein said disease associated with a decrease in bone mass is primary osteoporosis.

4. The method of treatment according to claim 3, wherein said primary osteoporosis is osteoporosis followed by aging, postmenopausal primary osteoporosis, or osteoporosis followed by ovariectomy.

5. The method according to claim 1 or 2, wherein said disease associated with a decrease in bone mass is secondary osteoporosis.

6. The method according to claim 5, wherein said secondary osteoporosis is glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, or rheumatoid osteoporosis.

7. The method according to claim 1 or 2, wherein said disease associated with a decrease in bone mass is metastatic bone, hypercalcemia, Paget's disease, bone loss, or osteonecrosis.

8. The method according to claim 1 or 2, wherein said disease associated with a decrease in bone mass is alveolar bone loss, mandibular bone loss, or childhood idiopathic bone loss.

9. The method according to claim 1 or 2, wherein said treatment of a disease associated with a decrease in bone mass is bone formation after fracture, bone formation after bone grafting, bone formation after operation of artificial joint, bone formation after spinal fusion, bone formation after bone regeneration, or alternative treatment for bone grafting.

* * * * *